United States Patent
Ren et al.

(10) Patent No.: US 11,674,961 B2
(45) Date of Patent: Jun. 13, 2023

(54) **EXTRACTION REAGENT FOR USE IN AN ASSAY FOR DETECTION OF GROUP A *STREPTOCOCCUS***

(71) Applicant: QUIDEL CORPORATION, San Diego, CA (US)

(72) Inventors: Peter Yan-Guo Ren, San Diego, CA (US); Stewart Hoelscher, San Diego, CA (US); Cristian Alberto, Chula Vista, CA (US); Stephanie Pinedo, San Diego, CA (US); Jason McClure, San Diego, CA (US); Hyunjin Kim, Beverly, MA (US)

(73) Assignee: Quidel Corporation, San Diego, CA (US)

( * ) Notice: Subject to any disclaimer, the term of this patent is extended or adjusted under 35 U.S.C. 154(b) by 223 days.

(21) Appl. No.: 16/600,295

(22) Filed: Oct. 11, 2019

(65) Prior Publication Data
US 2020/0116720 A1  Apr. 16, 2020

Related U.S. Application Data

(60) Provisional application No. 62/745,140, filed on Oct. 12, 2018.

(51) Int. Cl.
*G01N 33/569* (2006.01)
*G01N 33/532* (2006.01)

(52) U.S. Cl.
CPC ..... *G01N 33/56944* (2013.01); *G01N 33/532* (2013.01); *G01N 2400/10* (2013.01); *G01N 2469/10* (2013.01)

(58) Field of Classification Search
None
See application file for complete search history.

(56) References Cited

U.S. PATENT DOCUMENTS

| | | | |
|---|---|---|---|
| 7,582,729 B2 | 9/2009 | Fischetti et al. | |
| 7,838,255 B2 | 11/2010 | Fischetti et al. | |
| 9,034,322 B2 | 5/2015 | Fischetti et al. | |
| 9,914,915 B2 | 3/2018 | Fischetti et al. | |
| 10,544,407 B2 | 1/2020 | Fischetti et al. | |
| 2002/0058027 A1* | 5/2002 | Nelson | C12N 9/80 424/94.63 |
| 2008/0081341 A1* | 4/2008 | Maher | B01L 9/52 435/7.1 |
| 2011/0097723 A1* | 4/2011 | Liu | C12Q 1/6816 435/6.1 |
| 2011/0318755 A1 | 12/2011 | Piaso et al. | |
| 2013/0059290 A1* | 3/2013 | Armes | C12Q 1/6846 435/5 |
| 2013/0196337 A1 | 8/2013 | Ren et al. | |
| 2014/0072549 A1 | 3/2014 | Fischetti et al. | |
| 2017/0183714 A1* | 6/2017 | Shen | C12Q 1/6844 |
| 2017/0298334 A1 | 10/2017 | Fischetti et al. | |

FOREIGN PATENT DOCUMENTS

| | | |
|---|---|---|
| WO | WO 1988/002781 A1 | 4/1988 |
| WO | WO 2001/090331 A2 | 11/2001 |
| WO | WO 2010/039627 A2 | 4/2010 |
| WO | WO 2011/082309 A1 | 7/2011 |

OTHER PUBLICATIONS

Rudinger J. In: Peptide Hormones. (Ed) JA Parsons, University Park Press, pp. 1-7, 1976.*
Skolnick et al. Trends in Biotechnology 18: 34-39, 2000.*
DeCS document, Virual Health Sciences Descriptors, 1/1.. No publication date.*
Office rapid strep test: State of the art, pp. 1/8 to 8/8, Sep. 1, 2015.*
Sofia® QUIDEL Brochures, pp. 1-21, 2013.*
International Search Report from International Application No. PCT/US2019/055966, 5 pages, dated Feb. 21, 2020.
Nelson et al., "PlyC: a multimeric bacteriophage lysin", Proc. Natl. Acad. Sci. U.S.A., vol. 103, No. 28, pp. 10765-10770 (2006).

* cited by examiner

*Primary Examiner* — S. Devi
(74) *Attorney, Agent, or Firm* — McDermott Will & Emery LLP; Judy M. Mohr; Brennen P. Baylor

(57) ABSTRACT

An enzymatic extraction agent, as well as methods, compositions and kits for detecting Group A *Streptococcus* in a biological sample, which involve the enzymatic agent, are described.

27 Claims, 7 Drawing Sheets

EXTRACTION REAGENT FOR USE IN AN ASSAY FOR DETECTION OF GROUP A STREPTOCOCCUS

TECHNICAL FIELD

The present disclosure generally relates to the field of diagnostics, and, in particular, to devices, methods and kits for detecting analytes in biological samples. More particularly, the present disclosure provides an enzymatic extraction reagent and method to release *Streptococcus pyogenes* (Strep A, *S. pyogenes*, or Group A *Streptococcus*) antigens from the cell of Strep A. The exposed Strep A antigens, recognized by Strep A specific antibodies, can be used in combination with molecular assays or immunoassays to determine presence or absence of the bacterial antigen.

BACKGROUND

Strep A is a Gram-positive, non-motile, non-spore forming bacterium that occurs in chains or in pairs of cells, where individual cells are round-to-ovoid cocci, 0.6-1.0 micrometer in diameter. The cell surface structure of Strep A is composed of repeating units of N-acetylglucosamine and N-acetylmuramic acid, the standard peptidoglycan. Historically, the definitive identification of streptococci has rested on the serologic reactivity of "cell wall" polysaccharide antigens as originally described by Rebecca Lancefield. Eighteen group-specific antigens (Lancefield groups) were established. The Group A capsular polysaccharide (also called "C substance" or "group carbohydrate antigen") is a polymer of N-acetylglucosamine and rhamnose. Some group antigens are shared by more than one species. (K. Todar, Online Textbook of Bacteriology; See textbookofbacteriology.net).

*S. pyogenes* is one of the most frequent pathogens of humans. Approximately 5-15% of normal individuals harbor the bacterium, usually in the respiratory tract, yet remain asymptomatic. As normal flora, *S. pyogenes* can infect when defenses are compromised or when the organisms are able to penetrate the constitutive defenses. When the bacteria are introduced or transmitted to vulnerable tissues, a variety of types of suppurative infections can occur.

Acute diseases associated with *S. pyogenes* occur mainly in respiratory tract, bloodstream or skin. Streptococcal disease is most often a respiratory infection (pharyngitis or tonsillitis) or a skin infection (pyoderma). Acute *S. pyogenes* infections may present as pharyngitis (strep throat), scarlet fever (rash), impetigo (infection of the superficial layers of the skin) or cellulitis (infection of the deep layers of the skin). Invasive, toxigenic infections can result in necrotizing fasciitis, joint or bone infections, myositis, meningitis, endocarditis and streptococcal toxic shock syndrome. Patients may also develop immune-mediated post-streptococcal sequelae, such as acute rheumatic fever and acute glomerulonephritis, following acute infections caused by *S. pyogenes*, which occur in 1-3% of untreated infections. These conditions and their pathology are not attributable to dissemination of bacteria, but to aberrant immunological reactions to Strep A streptococcal antigens.

Because penicillin is effective in the treatment of Strep A streptococcal disease, the majority of infections amount to no more than pharyngitis accompanied by a rash. However, due to the occasional cases of rapidly progressive disease and because of the small risk of serious sequelae in untreated infections, *S. pyogenes* remains a major health concern, and efforts are being directed toward clarifying the risk and mechanisms of these sequelae and identifying rheumatogenic and nephritogenic strains of streptococci.

The cell surface of *S. pyogenes* accounts for many of the bacterium's determinants of virulence, especially those concerned with colonization and evasion of phagocytosis and the host immune responses. The surface of the bacterium is incredibly complex and chemically-diverse. Antigenic components include capsular polysaccharide (C-substance), cell wall peptidoglycan and lipoteichoic acid (LTA), and a variety of surface proteins, including M protein, fimbrial proteins, fibronectin-binding proteins, (e.g. Protein F) and cell-bound streptokinase.

The cytoplasmic membrane of *S. pyogenes* contains some antigens similar to those of human cardiac, skeletal, and smooth muscle, heart valve fibroblasts, and neuronal tissues. Molecular mimicry between pathogen and host has been proposed as a mechanism for the development of autoimmune diseases. Because microorganisms contain proteins similar to host proteins, the host's immune response may be suppressed or tolerant to infection. Conversely, stimulation of the host's B and T cells by a molecular mimic can cause the host's immune system to begin responding to self proteins as if they are foreign.

As in other autoimmune diseases, both environmental and genetic factors are involved in the development of rheumatic carditis and inflammatory heart disease, and molecular mimicry between the Strep A *Streptococcus* and heart tissues appears to play a role. The study of B and T cell responses against Strep A streptococcal antigens has yielded some information about several steps in the pathogenesis of rheumatic carditis following Strep A streptococcal infection. An early step involves the development of cross-reactive autoantibodies against the Strep A streptococcal carbohydrate antigen N-acetyl-glucosamine and cardiac myosin. These antibodies then react with valvular endothelium, which becomes inflamed with expression of vascular cell adhesion molecule-1 (VCAM-1). T cells, CD4+ and CD8+, then infiltrate through the endothelium/endocardium into the valve (an avascular structure). Aschoff bodies or granulomatous lesions may form containing macrophages and T cells underneath the endocardium. The T cells are responsive to streptococcal M protein antigen sequences. The valve becomes scarred with eventual neovascularization and progressive, chronic disease in the valve. In the host, the mimicking antigens cardiac myosin and laminin have been involved in the myocardium and valve, respectively. (Cunningham, *Front. Biosci.*, 2003, 8:s533-43).

Rheumatic fever (RF) and the antiphospholipid syndrome (APS) are autoimmune diseases sharing similar cardiac and neurological pathologies. There appears to be a considerable overlap of humoral immunity in RF and APS, supporting a hypothesis that common pathogenic mechanisms underlie the development of cardiac valve lesions and Central Nervous System abnormalities in both diseases. The pathogenic molecules engaged in these autoimmune conditions, M protein, N-acetyl-beta-D-glucosamine (also called "NAG" or "GlcNAc") and beta2 glycoprotein-I (beta2GPI), were found to share some epitopes. The immunoglobulin G sera from APS patients contained a considerable anti-streptococcal M protein as well as anti-GlcNAc activity. Furthermore, beta2GPI inhibited anti-GlcNAc activity from APS patients with chorea. (Blank, et al., 2006, *Rheumatology* (Oxford). 45(7):833-41).

Detection of microbial pathogens in biological samples is of particular value in clinical medicine, as treatment may vary considerably depending upon the causative organism. Thus, the accurate and rapid identification of pathogens in biological samples of patients suspected of having an infectious disease can be critical to provide prompt and appropriate treatment to patients. Rapid identification of disease-causing organisms in biological samples is important even for non-life threatening infections.

Rapid methods of diagnosing microbial infections have been developed to provide timely results for guiding clinical therapy. Some of the most effective of these rapid methods have been immunologically based. Monoclonal and polyclonal antibodies to microbe-specific antigens have been developed and used in immunoassays to identify specific microbes in biological samples. For example, immunoassays for the identification of Strep A streptococcal antigens in human samples are useful for the early detection of *S. pyogenes* infection, so that proper antibiotic treatment may be started.

Strep A *Streptococcus* in pharyngeal exudates can be identified by polyclonal or monoclonal antibodies to antigens specific for Group A *Streptococcus*. One such test is described in U.S. Pat. No. 5,770,460, providing a one-step lateral flow assay for Strep A *Streptococcus*-specific antigens. However, tests relying on pharyngeal swabs are often complicated by a high false positive rate. Although instructions for use of pharyngeal swab tests specifically direct the user to avoid contacting the tongue, cheek and/or teeth with the swab, inadvertent contact often occurs, nonetheless. Epithelial cells originating from the tongue, cheek and/or teeth may contain molecular mimics of one or more components of the *S. pyogenes* cell wall, and the polyclonal or monoclonal antibody specific for Strep A *Streptococcus* may bind and "recognize" epitopes on the epithelial cells in a test subject not infected by or carrying Group A strep, resulting in a false positive result. U.S. Application Publication No. 2013/0196337, incorporated by reference in its entirety, discloses a highly specific and facile immunoassay with a reduced rate of false positives, providing accurate detection of Strep A *Streptococcus* infection. The immunoassay in which the specificity of detection of Strep A *Streptococcus* is enhanced by addition of a reagent that blocks binding of the antibody or binding member in the immunoassay that binds Group A *Streptococcus* antigen to epithelial cell wall glycoproteins that may be present in the sample. Exemplary reagents are referred to herein as a 'blocking reagent' and include N-acetyl-D-glucosamine (NGA) glucosamine, acetyl-galactosamine, galactosamine, mannosamine, acetylmuramic acid, chitin, chitosan and hyaluronic acid.

Previous immunoassays treat the biological sample suspected of containing Strep A *Streptococcus* infection with a chemical agent to expose and release Strep A antigens, if any, from the cell for binding with Strep A specific antibodies. The present disclosure provides an enzymatic extraction of the antigenic compounds from Strep A bacterial for immunoassay.

Comparing with chemical extraction which is conducted in an acidic condition (the pH is usually between about 3 and 4.5), the enzymatic extraction method disclosed herein is conducted under a pH neutral (the pH is about 6-8) condition which favors both processes of Strep A antigen extraction and Strep A antibody-antigen interaction. The enzymatic extraction method disclosed herein does not require neutralization step to adjust the pH range of the extraction sample for Strep A antibody-antigen interaction, before or during the signal detection in an assay device. The assay using enzymatic extraction method disclosed herein therefore can make possible for more efficient antigen extraction and more sensitive detection than an assay using chemical extraction.

BRIEF SUMMARY

The present disclosure provides devices, methods and diagnostic kits for detecting Strep A in biological samples. More particularly, the present disclosure provides an assay, immunoassay or molecular assay, in which the biological sample is treated with a bacteriophage lysin to release Strep A antigens from the bacterial cell.

In a first aspect, an enzymatic extraction agent, in the form of a lyophilized or dried composition or in the form of an aqueous composition, comprising PlyC or a derivative thereof (such as a recombinant PlyCA or recombinant PlyCB mutant) is provided.

In some embodiments, the lyophilized or dried composition further comprises a salt, a sugar (sucrose and/or trehalose), a carrier protein (such as casein and/or methylated BSA), and/or detergents. In some embodiments, the lyophilized or dried composition even further comprises an antibody (polyclonal/monoclonal) specific to Strep A antigens coupled with microbeads (europium chelate-impregnated microbeads, or colored or magnetic microbeads) or gold sol, or carbon microparticles.

In one embodiment, the lyophilized or dried composition comprising PlyC or a derivative thereof can be prepared by lyophilizing an enzymatic extraction agent in the form of an aqueous composition comprising, in addition to PlyC or a derivative thereof in the amount ranging from 0.1 to 80 μg/mL, a salt to maintain the pH in the range of 6-8, a sugar (such as sucrose and/or trehalose), a carrier protein (such as casein and/or methylated BSA), and/or detergents. In some embodiments, the aqueous composition can further comprise an antibody (polyclonal/monoclonal) specific to Strep A antigens coupled with microbeads (europium chelate-impregnated microbeads, i.e., microparticles dyed with a fluorescent europium compound, or colored or magnetic microbeads) or gold sol, or carbon microparticles. In some embodiments, the antibody (polyclonal/monoclonal) specific to Strep A antigens coupled with microbeads are placed in the lyophilized or dried composition comprising PlyC or a derivative thereof.

In another aspect, an enzymatic extraction method for obtaining a Strep A-specific antigen from a biological sample containing or suspected of containing Strep A is provided. The method comprises mixing the biological sample with an aqueous composition comprising PlyC or a derivative thereof.

In some embodiments, the aqueous composition comprises PlyC or a derivative thereof is obtained by rehydrating the lyophilized or dried composition comprising PlyC or a derivative thereof as disclosed herein with a buffered solution, water, or transfer medium.

In some embodiments, the method comprises eluting the biological sample into a transfer medium followed by mixing the transfer medium with the lyophilized or dried composition comprising PlyC or a derivative thereof as disclosed herein.

In some embodiments, the method further comprises incubating the resulting extraction mixture for a period of between about 1 to 10 minutes. The extracted mixture can then be applied on an immunoassay device as the antigen source.

In another aspect, a device for detecting the presence of Group A *Streptococcus* in a biological sample is provided. The device comprises a matrix having (i) a sample receiving zone for receiving a sample containing or suspected of containing a Strep A-specific antigen ("Strep A-specific antigen sample"), wherein the Strep A-specific antigen sample is obtained by the enzymatic extracting method disclosed herein, (ii) a labeling zone containing an antibody for specifically labeling the antigen as it passes there through and (iii) a capture zone having means for specifically binding the labeled antigen thereon, wherein the sample receiving zone, the labeling zone and the capture zone are arranged on the matrix in a liquid flow path. In some embodiments, at least one of the sample receiving zone and the labeling zone and the extraction reagent comprise a blocking reagent. In one embodiment, the blocking reagent is N-acetyl-D-glucosamine (NAG).

In one embodiment, the antibody is a polyclonal antibody or monoclonal antibody.

In another embodiment, the antibody is fluorescently labeled. For example, the antibody is coated on microparticles dyed with a fluorescent europium compound. That is to say, the antibody is in the form of the antibody-tagged microparticles dyed with a fluorescent europium compound.

In still another embodiment, the means for specifically binding the labeled antigen is a capture antibody. In one embodiment, the capture antibody is a polyclonal antibody or monoclonal antibody.

In another aspect, an assay for detecting the presence or absence of Group A *Streptococcus* in a biological sample is provided. The assay comprises an enzymatic extraction agent as described herein, and a container comprising deoxyribose nucleotide triphosphates (dNTPs) and a forward primer, a reverse primer and a probe, the primers and the probe specific for a target sequence of Group A *Streptococcus*.

In one embodiment, the assay further comprises a reagent for isothermal amplification of the Group A *Streptococcus* target. In one embodiment, the reagent comprises an enzyme for helicase dependent amplification.

In another embodiment, the assay further comprises a reagent for the amplification of the Group A *Streptococcus* target. In one embodiment, the reagent comprises an enzyme for amplification.

In another aspect, a kit is provided. The kit comprises a device comprising a matrix having (i) a sample receiving zone for receiving a Strep A-specific antigen sample, (ii) a labeling zone containing an antibody for specifically labeling the antigen as it passes there through and (iii) a capture zone having means for specifically binding the labeled antigen thereon, wherein the sample receiving zone, the labeling zone and the capture zone are arranged on the matrix in a liquid flow path; and a container comprising an extraction reagent as disclosed herein. In some embodiments, at least one of the extraction reagent, the sample receiving zone and the labeling zone comprise a blocking reagent, such as N-acetyl-D-glucosamine (NAG).

In one embodiment, the blocking reagent is deposited on the sample receiving zone.

In another aspect, a method for detecting the presence or absence of Strep A in a biological sample is provided. The method comprises providing a device or a kit as described herein placing a Strep A-specific antigen sample on the device; and determining the presence or absence of Strep A, for example by visually reading (with the unaided eye, with an instrument, or with the eye assisted by an instrument) the result on the test line of the device.

In one embodiment, the method further comprises providing an instrument for collecting a biological sample; and collecting a biological sample on the instrument.

In still another embodiment, the method further comprises providing instructions for use, wherein the instructions do not caution to not touch the tongue, sides or top of mouth with the instrument when collecting the sample.

In another aspect, a kit is provided. The kit comprises a device or assay according to any of the embodiments described herein, a container comprising an enzymatic extraction agent as disclosed herein; and an instrument for collecting a Strep A-specific antigen sample; and instructions for use.

In one embodiment, the instrument is a swab.

In another embodiment, the instructions do not caution to not touch the tongue, sides or top of mouth with the instrument when collecting the sample.

In one embodiment, a device for detecting the presence of Group A *Streptococcus* in a sample is provided. The device comprises a receiving chamber for receiving a biological sample suspected of comprising Strep A, the chamber dimensioned to receive a liquid enzymatic extraction agent as disclosed herein; and a matrix having a sample receiving zone for receiving the treated sample, a labeling zone having a labelled polyclonal or monoclonal antibody for specifically labeling the antigen as it passes there through and a capture zone having means for specifically binding the labeled antigen thereon, wherein the sample receiving zone, the labeling zone and the capture zone are arranged on the matrix in a liquid flow path. In some embodiments, the chamber is dimensioned to receive both the liquid extraction reagent as disclosed herein and a blocking reagent that inhibits or blocks binding of the antibody with human epithelial cell wall glyoproteins present in the sample. These reagents combine with the sample to form a treated sample.

In another embodiment, a method for detecting the presence of Group A *Streptococcus* in a sample is provided. The method comprises providing a matrix having (i) a sample receiving zone for receiving a Strep A-specific antigen sample, (ii) a labeling zone containing an antibody for specifically labeling the antigen as it passes there through and (iii) a capture zone having means for specifically binding the labeled antigen thereon, wherein the sample receiving zone, the labeling zone and the capture zone are arranged on the matrix in a liquid flow path, and contacting the sample receiving zone with the sample, wherein said sample is treated with a liquid reagent comprising the enzymatic extraction agent as disclosed herein prior to contacting; and detecting the presence or absence of the antigen in the capture zone. In some embodiments, the liquid reagent further comprises a blocking reagent, such as N-acetyl-D-glucosamine (NAG).

In another embodiment, a device for detecting the presence of Group A *Streptococcus* in a sample is provided. The device comprises a receiving chamber for receiving a Strep A-specific antigen sample, the chamber dimensioned to receive a liquid enzymatic extraction agent as disclosed herein that contacts the sample to provide a treated sample; and a matrix having a sample receiving zone for receiving the treated sample, a labeling zone containing a polyclonal or monoclonal antibody for specifically labeling the antigen as it passes there through and a capture zone having means for specifically binding the labeled antigen thereon, wherein the sample receiving zone, the labeling zone and the capture zone are arranged on the matrix in a liquid flow path. In some embodiments, the labeling zone further contains a blocking reagent, such as N-acetyl-D-glucosamine (NAG).

In yet another embodiment, a device for detecting the presence of Group A *Streptococcus* in a sample is provided. The device comprises a receiving chamber for receiving a Strep A-specific antigen sample, the chamber dimensioned to receive a liquid enzymatic extraction agent that contacts the sample to provide a treated sample; and a matrix having a sample receiving zone for receiving the treated sample, a labeling zone containing a polyclonal antibody for specifically labeling the antigen as it passes there through and a capture zone containing a means for specifically binding the labeled antigen thereon, wherein the sample receiving zone, the labeling zone and the capture zone are arranged on the matrix in a liquid flow path. In some embodiment, the capture zone further contains a blocking reagent, such as N-acetyl-D-glucosamine (NAG).

In still another embodiment, a method to reduce the false positive rate of a lateral flow assay in the detection of Group A *Streptococcus* in a sample is provided, where in the lateral flow assay, N-acetyl-D-glucosamine (NAG)-binding components of a polyclonal antibody label used in the assay are preferentially bound. The method comprises adding to an enzymatic extraction agent as disclosed herein, or to a localized region of the immunoassay test strip, an amount of N-acetyl-D-glucosamine (NAG) effective as a blocking agent to enhance the specific binding of the polyclonal antibody to Group A *Streptococcus* antigen and reduce the false positive rate of the assay.

In the embodiments when the enzymatic extraction agent further comprising an antibody (polyclonal/monoclonal) specific to Strep A antigens coupled with microbeads (europium chelate-impregnated microbeads, or colored or magnetic microbeads) or gold sol, or carbon microparticles is used to extract and release Strep A antigens from the cell, the labeling zone in the device is not needed.

Thus, in yet another embodiment, a device for detecting the presence of Group A *Streptococcus* in a sample is provided. The device comprises a receiving chamber for receiving a Strep A-specific antigen sample, the chamber dimensioned to receive a liquid enzymatic extraction agent that contacts the sample to provide a treated sample, wherein the liquid enzymatic extraction agent comprises an antibody (polyclonal/monoclonal) specific to Strep A antigens coated on fluorescent microparticles for the formation of a labeled Strep A antigen (i.e, a complex of the Strep A antigen and the antibody coated on fluorescent microparticles); and a matrix having a sample receiving zone for receiving the treated sample, and a capture zone containing a means for specifically binding the labeled antigen thereon, wherein the sample receiving zone and the capture zone are arranged on the matrix in a liquid flow path. In some embodiment, the capture zone further contains a blocking reagent, such as N-acetyl-D-glucosamine (NAG)

The following aspects and embodiments thereof described and illustrated below are meant to be exemplary and illustrative, not limiting in scope.

Figure 1:
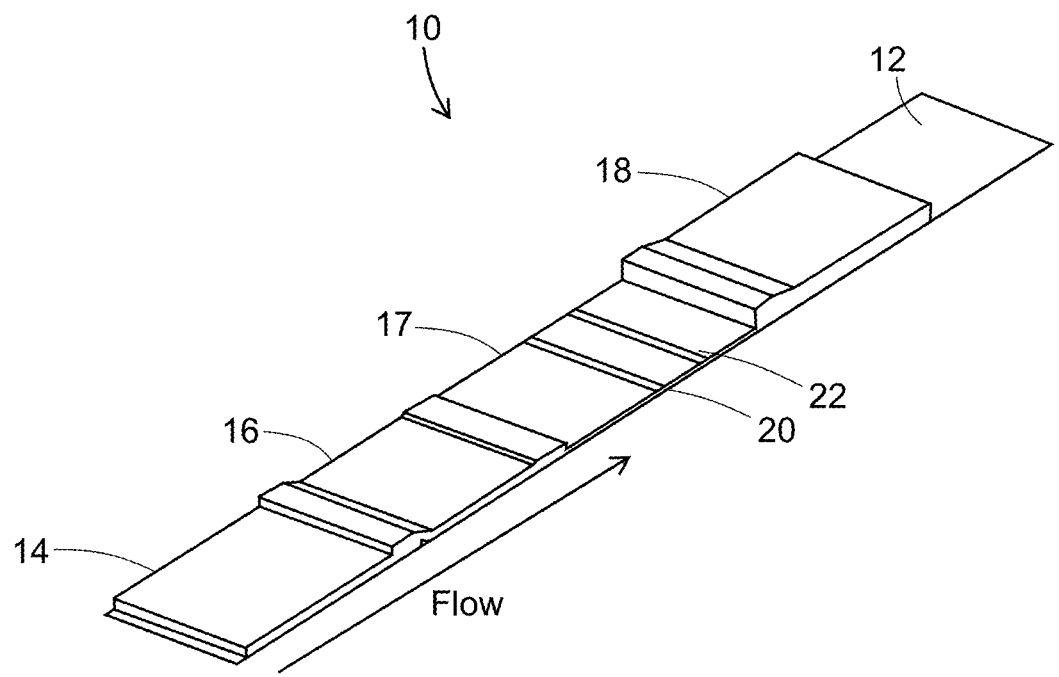
FIG. 1 illustrates an exemplary immunoassay device.

These and other embodiments are further described in the detailed description that follows.

DETAILED DESCRIPTION

I. Definitions

Before the present methods and compositions are described, it is to be understood that this disclosure is not limited to particular embodiments described, as such may, of course, vary. Several embodiments of the present disclosure are described in detail hereinafter. These embodiments may take many different forms and should not be construed as limited to those embodiments explicitly set forth herein. Rather, these embodiments are provided so that this disclosure will be thorough and complete, and will fully convey the scope of the present disclosure to those skilled in the art. It is also to be understood that the terminology used herein is for the purpose of describing particular embodiments only, and is not intended to be limiting, since the scope of the invention will be limited only by the appended claims.

All patents, applications, published applications and other publications referred to herein are incorporated by reference in their entirety.

As used herein, the following terms are intended to have the following meanings:

As used herein, the singular forms "a," "an," and "the" include plural referents unless the context clearly dictates otherwise. Thus, for example, reference to "a protein" includes a plurality of such proteins and reference to "the formulation" includes reference to one or more formulations and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed by this disclosure. The upper and lower limits of these smaller ranges may independently be included or excluded in the range, and each range where either, neither or both limits are included in the smaller ranges is also encompassed by this disclosure, subject to any specifically excluded limit in the stated range. Where the stated range includes one or both of the limits, ranges excluding either or both of those included limits are also within the scope of this disclosure.

"Protein," "polypeptide," "oligopeptide," and "peptide" are used interchangeably to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

N-Acetylglucosamine (also called "N-acetyl-D-glucosamine," "NAG" or "GlcNAc") is a monosaccharide derivative of glucose having a molecular formula of $C_8H_{15}NO_6$, a molar mass of 221.21 g/mol. It is part of a biopolymer in bacterial cell walls, and, in particular, the cell surface structure of *Streptococcus pyogenes* (Group A *Streptococcus*) comprises alternating units of NAG and N-acetylmuramic acid (MurNAc), cross-linked with oligopeptides at the lactic acid residue of MurNAc. This layered structure is called peptidoglycan. NAG is the monomeric unit of the polymer chitin, which forms the exoskeletons of insects and crustaceans. NAG polymerized with glucuronic acid forms hyaluronan, a component of connective, epithelial and neural tissues of higher organisms.

The term "sequence identity" means nucleic acid or amino acid sequence identity in two or more aligned sequences, aligned using a sequence alignment program.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at (ncbi.nlm.gov/BLAST/). See, also, Altschul, S. F. et al., 1990 and Altschul, S. F. et al., 1997.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 3389-3402, respectively. Software for performing BLAST analyses is publicly available through the National Center for Biotechnology Information website. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci.* USA 89:10915 (1989)).

While all of the above mentioned algorithms and programs are suitable for a determination of sequence alignment and % sequence identity, for purposes of the disclosure herein, determination of % sequence identity will typically be performed using the BESTFIT or GAP programs in the GCG Wisconsin Software package (Accelrys, Madison Wis.), using default parameters provided.

The phrase "% sequence identity" refers to the level of nucleic acid or amino acid sequence identity between two or more aligned sequences, when aligned using a sequence alignment program. For example, 70% homology means the same thing as 70% sequence identity determined by a defined algorithm, and accordingly a homologue of a given sequence has greater than 70% sequence identity over a length of the given sequence. Exemplary levels of sequence identity include, but are not limited to 70%, 75% 80%, 85%, 90% or 95%, 96%, 97%, 98% or 99% sequence identity to a given sequence, e.g., the nucleic acid or amino acid sequence of a protein, as described herein.

"Associated" refers to coincidence with the development or manifestation of a disease, condition or phenotype. Association may be due to, but is not limited to, genes responsible for housekeeping functions whose alteration can provide the foundation for a variety of diseases and conditions, those that are part of a pathway that is involved in a specific disease, condition or phenotype and those that indirectly contribute to the manifestation of a disease, condition or phenotype.

As pertains to the present disclosure, a biological fluid can be a solid, or semi-solid sample, including feces, biopsy specimens, skin, nails, and hair, or a liquid sample, such as urine, saliva, sputum, mucous, blood, blood components such as plasma or serum, amniotic fluid, semen, vaginal secretions, tears, spinal fluid, washings, and other bodily fluids. Included among the sample are swab specimens from, e.g., the cervix, urethra, nostril, and throat. Any of such samples may be from a living, dead, or dying animal or a plant. Animals include mammals, such as humans.

"Antibody" refers to a polypeptide substantially encoded by an immunoglobulin gene or immunoglobulin genes, or fragments thereof. The recognized immunoglobulin genes include the kappa, lambda, alpha, gamma, delta, epsilon, and mu constant regions, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, an antibody is an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof. Fragments thereof may include Fab, Fv and F(ab')2, Fab', and the like. Antibodies may also include chimeric antibodies or fragment thereof made by recombinant methods.

"Antibody" includes whole antibodies, including those of the IgG, IgM and IgA isotypes, and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The IgG heavy chain constant region is comprised of four domains, CH1, hinge, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

"Isolated antibody," as used herein, is intended to refer to an antibody which is substantially free of other antibodies having different antigenic specificities (e.g., an isolated antibody that specifically binds to the protein of interest is substantially free of antibodies that specifically bind antigens other than the protein of interest). An isolated antibody that specifically binds to an epitope, isoform or variant of the protein of interest may, however, have cross-reactivity to other related antigens, e.g., from other species (e.g., species homologs). Moreover, an isolated antibody may be substantially free of other cellular material and/or chemicals. In some embodiments, a combination of "isolated" monoclonal antibodies having different specificities are combined in a well-defined composition.

"Specific binding" refers to antibody binding to a predetermined antigen. Typically, the antibody binds with a dissociation constant (KD) of $10^{-7}$ M or less, and binds to the predetermined antigen with a KD that is at least two-fold less than its KD for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

"Immunological binding," as used herein, generally refers to the non-covalent interactions of the type that occurs between an antibody, or fragment thereof, and the type 1 interferon or receptor for which the antibody is specific. The strength, or affinity, of immunological binding interactions can be expressed in terms of the dissociation constant (Kd) of the interaction, wherein a smaller Kd represents a greater affinity. Immunological binding properties of selected antibodies can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" (Kon) and the "off rate constant" (Koff) can be determined by calculation of the concentrations and the actual rates of association and dissociation. The ratio of Koff/Kon enables cancellation of all parameters not related to affinity, and is thus equal to the dissociation constant Kd. See, generally, Davies et al., Annual Rev. Biochem. 59:439-473 (1990).

"High affinity" for an IgG antibody refers to an antibody having a KD of $10^{-8}$ M or less, more preferably $10^{-9}$ M or less and even more preferably $10^{-10}$ M or less. However, "high affinity" binding can vary for other antibody isotypes. For example, "high affinity" binding for an IgM isotype refers to an antibody having a KD of $10^{-7}$ M or less, more preferably $10^{-8}$ M or less.

Monoclonal antibodies to a compound may be prepared using any technique which provides for the production of antibody molecules by continuous cell lines in culture. These include, but are not limited to, the hybridoma technique originally described by Kohler & Milstein, 1975, Nature 256:495-497 and/or Kaprowski, U.S. Pat. No. 4,376,110; the human B-cell hybridoma technique described by Kosbor et al., 1983, Immunology Today 4:72 and/or Cote et al., 1983, Proc. Natl. Acad. Sci. USA 80:2026-2030; and the EBV-hybridoma technique described by Cole et al., 1985, Monoclonal Antibodies and Cancer Therapy, Alan R. Liss, Inc., pp. 77-96. In addition, techniques developed for the production of "chimeric antibodies" (Morrison et al., 1984, Proc. Natl. Acad. Sci. USA 81:6851-6855; Neuberger et al., 1984, Nature 312:604-608; Takeda et al., 1985, Nature 314:452-454; Boss, U.S. Pat. No. 4,816,397; Cabilly, U.S. Pat. No. 4,816,567) by splicing the genes from a mouse antibody molecule of appropriate antigen specificity together with genes from a human antibody molecule of appropriate biological activity can be used. Or "humanized" antibodies can be prepared (see, e.g., Queen, U.S. Pat. No. 5,585,089). Alternatively, techniques described for the production of single chain antibodies (see, e.g., U.S. Pat. No. 4,946,778) can be adapted to produce compound-specific single chain antibodies.

Antibody fragments which contain deletions of specific binding sites may be generated by known techniques. For example, such fragments include but are not limited to F(ab')2 fragments, which can be produced by pepsin digestion of the antibody molecule and Fab fragments, which can be generated by reducing the disulfide bridges of the F(ab')2 fragments. Alternatively, Fab expression libraries may be constructed (Huse et al., 1989, Science 246:1275-1281) to allow rapid and easy identification of monoclonal Fab fragments with the desired specificity for the peptide of interest.

The antibody or antibody fragment specific for the desired peptide can be attached, for example, to agarose, and the antibody-agarose complex is used in immunochromatography to purify peptides. See, Scopes, 1984, Protein Purification: Principles and Practice, Springer-Verlag New York, Inc., N.Y., Livingstone, 1974, Methods In Enzymology: Immunoaffinity Chromatography of Proteins 34:723-731.

"Detect" and "detection" have their standard meaning, and are intended to encompass detection, measurement and/or characterization of a selected protein or protein activity. For example, enzyme activity may be "detected" in the course of detecting, screening for, or characterizing inhibitors, activators, and modulators of the protein.

The term "reference level" refers to a detected level of a positive or negative control. For example, a reference level of a positive control can be a known amount of Strep A-specific antigen, obtained from a sample or culture of a known Strep A bacterium, a subject known to be infected with Strep A, or can refer to a numerical value derived from known sources of Group A *Streptococcus*-specific antigen.

"Label" refers to any moiety that, when attached to a moiety described herein, e.g., a peptide, protein or antibody, renders such a moiety detectable using known detection methods, e.g., spectroscopic, photochemical, electrochemi-luminescent, and electrophoretic methods. Various labels suitable for use in the present disclosure include labels which produce a signal through either chemical or physical means, wherein the signal is detectable by visual or instrumental means. Exemplary labels include, but are not limited to, fluorophores and radioisotopes. Such labels allow direct detection of labeled compounds by a suitable detector, e.g., a fluorometer. Such labels can include enzymes and substrates, chromogens, catalysts, fluorescent compounds, phosphorescent compounds, chemiluminescent compounds, and radioactive labels. Typically, a visually detectable label is used, thereby providing for instrumental (e.g. spectrophotometer) readout of the amount of the analyte in the sample. Labels include enzymes such as horseradish peroxidase, galactosidase (alpha and/or beta), and alkaline phosphatase. Suitable substrates include 3,3',5,5'-tetramethylbenzidine (TMB) and 1,2 dioxetane. The method of detection will depend upon the labeled used, and will be apparent to those of skill in the art. Examples of suitable direct labels include radiolabels, fluorophores, chromophores, chelating agents, particles, chemiluminescent agents and the like.

For such embodiments, the label may be a direct label, i.e., a label that itself is detectable or produces a detectable signal, or it may be an indirect label, i.e., a label that is detectable or produces a detectable signal in the presence of another compound. "Labeled second antibody" refers to an antibody that is attached to a detectable label. The label allows the antibody to produce a detectable signal that is related to the presence of analyte in the fluid sample.

Radioactive labels: Suitable radiolabels include, by way of example and not limitation, $^{3}H$, $^{14}C$, $^{32}P$, $^{35}S$, $^{36}Cl$, $^{57}Co$, $^{131}I$ and $^{186}Re$.

"Chromophore" refers to a moiety with absorption characteristics, i.e., are capable of excitation upon irradiation by any of a variety of photonic sources. Chromophores can be fluorescing or non-fluorescing, and includes, among others, dyes, fluorophores, luminescent, chemiluminescent, and electrochemiluminescent molecules.

Examples of suitable indirect labels include enzymes capable of reacting with or interacting with a substrate to produce a detectable signal (such as those used in ELISA and EMIT immunoassays), ligands capable of binding a labeled moiety, and the like. Suitable enzymes useful as indirect labels include, by way of example and not limitation, alkaline phosphatase, horseradish peroxidase, lysozyme, glucose-6-phosphate dehydrogenase, lactate dehydrogenase and urease. The use of these enzymes in ELISA and EMITimmunoassays is described in detail in Engvall, 1980, *Methods Enzym.* 70: 419-439 and U.S. Pat. No. 4,857,453.

"Substrate," "support," "solid support," "solid varrier," or "resin" are interchangeable terms and refer to any solid phase material. Substrate also encompasses terms such as "solid phase," "surface," and/or "membrane." A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. "Solid support" includes membranes (e.g. nitrocellulose), microtiter plate (e.g. PVC, polypropylene, polystyrene), dipstick, test tube, and glass or plastic beads. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments. Methods for immobilizing biomolecules are well known in the art, and the antibody can be attached covalently or non-covalently. In one embodiment, the solid support is a stretavidin coated plate to which a biotinylated antibody is non-covalently attached.

In statistics and diagnostic testing, sensitivity and specificity are statistical measures of the performance of a binary classification test. Sensitivity (also called "recall rate") measures the proportion of actual positives which are correctly identified as such (e.g. the percentage of sick people who are correctly identified as having the condition). Specificity measures the proportion of negatives which are correctly identified (e.g. the percentage of healthy people who are correctly identified as not having the condition). These two measures are closely related to the concepts of type I and type II errors. A theoretical, optimal prediction aims to achieve 100% sensitivity (i.e. predict all people from the sick group as sick) and 100% specificity (i.e. not predict anyone from the healthy group as sick), however theoretically any predictor will possess a minimum error bound known as the Bayes error rate.

"Specificity" relates to the ability of the diagnostic test to identify negative results.

$$\text{Specificity} = \frac{\text{\# of True Negatives}}{(\text{\# of True Negatives} + \text{\# of False Positives})}$$

If a test has high specificity, a positive result from the test means a high probability of the presence of the disease for which the test is testing.

"Sensitivity" relates to the ability of the diagnostic test to identify positive results.

$$\text{Sensitivity} = \frac{\text{\# of True Positives}}{(\text{\# of True Positives} + \text{\# of False Negatives})}$$

If a test has high sensitivity then a negative result would suggest the absence of disease. For example, a sensitivity of 100% means that the test recognizes all actual positives—i.e. all sick people are recognized as being ill. Thus, in contrast to a high specificity test, negative results in a high sensitivity test are used to rule out the disease.

For any test, there is usually a trade-off between the measures. For example: in an airport security setting in which one is testing for potential threats to safety, scanners may be set to trigger on low-risk items like belt buckles and keys (low specificity), in order to reduce the risk of missing objects that do pose a threat to the aircraft and those aboard (high sensitivity). This trade-off can be represented graphically using a receiver operating characteristic (ROC) curve.

In some embodiments, a ROC is used to generate a summary statistic. Some common versions are: the intercept of the ROC curve with the line at 90 degrees to the no-discrimination line (also called Youden's J statistic); the area between the ROC curve and the no-discrimination line; the area under the ROC curve, or "AUC" ("Area Under Curve"), or A' (pronounced "a-prime"); d' (pronounced "d-prime"), the distance between the mean of the distribution of activity in the system under noise-alone conditions and its distribution under signal-alone conditions, divided by their standard deviation, under the assumption that both these distributions are normal with the same standard deviation. Under these assumptions, it can be proved that the shape of the ROC depends only on d'.

The "positive predictive value (PPV)," or "precision rate" of a test is a summary statistic used to describe the proportion of subjects with positive test results who are correctly diagnosed. It is a measure of the performance of a diagnostic method, as it reflects the probability that a positive test reflects the underlying condition being tested for. Its value does however depend on the prevalence of the outcome of interest, which may be unknown for a particular target population. The PPV can be derived using Bayes' theorem.

The PPV is defined as:

$$PPV = \frac{\text{\# of True Positives}}{(\text{\# of True Positives} + \text{\# of False Positives})} = \frac{\text{\# of True Positives}}{\text{\# of Positive calls}}$$

where a "true positive" is the event that the test makes a positive prediction, and the subject has a positive result under the gold standard, and a "false positive" is the event that the test makes a positive prediction, and the subject has a positive result under the gold standard.

"Negative predictive value (NPV)" is defined as the proportion of subjects with a negative test result who are correctly diagnosed. A high NPV means that when the test yields a negative result, it is uncommon that the result should have been positive. In the familiar context of medical testing, a high NPV means that the test only rarely misclassifies a sick person as being healthy. Note that this says nothing about the tendency of the test to mistakenly classify a healthy person as being sick.

The NPV is determined as:

$$NPV = \frac{\text{\# of True Negatives}}{(\text{\# of True Negatives} + \text{\# of False Negatives})} = \frac{\text{\# of True Negatives}}{\text{\# of Negative calls}}$$

where a "true negative" is the event that the test makes a negative prediction, and the subject has a negative result under the gold standard, and a "false negative" is the event that the test makes a negative prediction, and the subject has a positive result under the gold standard.

If the prevalence, sensitivity, and specificity are known, the positive and negative predictive values (PPV and NPV) can be calculated for any prevalence as follows:

$$PPV = \frac{\text{sensitivity} \times \text{prevalence}}{\text{sensitivity} \times \text{prevalence} + (1 - \text{specificity}) \times (1 - \text{prevalence})}$$

$$NPV = \frac{\text{specificity} \times (1 - \text{prevalence})}{(1 - \text{sensitivity}) \times \text{prevalence} + \text{specificity} \times (1 - \text{prevalence})}$$

If the prevalence of the disease is very low, the positive predictive value will not be close to 1 even if both the sensitivity and specificity are high. Thus in screening the general population it is inevitable that many people with positive test results will be false positives.

The rarer the abnormality, the more sure one can be that a negative test indicates no abnormality, and the less sure that a positive result really indicates an abnormality. The prevalence can be interpreted as the probability before the test is carried out that the subject has the disease, known as the prior probability of disease. The positive and negative predictive values are the revised estimates of the same probability for those subjects who are positive and negative on the test, and are known as posterior probabilities. The difference between the prior and posterior probabilities is one way of assessing the usefulness of the test.

For any test result we can compare the probability of getting that result if the patient truly had the condition of interest with the corresponding probability if he or she were healthy. The ratio of these probabilities is called the likelihood ratio, calculated as sensitivity/(1−specificity). (Altman D G, Bland J M (1994). "Diagnostic tests 2: Predictive values", *BMJ* 309 (6947):102).

"Rule-out criteria" "Rule-Out," or "RO" are terms used in a medical differential diagnosis of a disease or condition, in which certain criteria are evaluated in a clinical decision-making process of elimination or inclusion. A subject is "ruled-out" when, upon consideration of the criteria, the subject has been determined not to have met all or a significant number of criteria for having a disease.

II. Devices and Kits Comprising the Enzymatic Extraction Agent and Methods of Use Assays and diagnostic kits for detecting the presence or absence of Strep A in a biological sample are provided. The assay, which can be an immunoassay or molecular assay, comprises an extraction reagent for treating the biological sample to release Strep A antigens from the bacterial cell, if Strep A is present in the sample. The extraction reagent comprises a bacteriophage lysin, as will now be described.

In one embodiment, the bacteriophage lysin is PlyC. PlyC, a streptococcal C1 bacteriophage lysin, is one of the most potent peptidoglycan hydrolases. PlyC is a bacteriophage-encoded, multimeric lysin composed of two distinct gene products, PlyCA and PlyCB. A single PlyCA protein binds to the octamer PlyCB to form the functional holoenzyme of PlyC. The PlyCA molecule is responsible for the enzymatic activity while a self-assembled ring-shaped assembly of eight PlyCB molecules is involved in the streptococcal cell-wall-specific binding.

PlyC lyses the cell walls of the *Streptococcus pyogenes* (Strep A) on contact resulting in the exposure and release of Strep A antigens from the cell. The exposed Strep A antigens can be recognized by Strep A specific antibodies, which can be used in combination with immunoassays (such as ELISA, lateral flow assays) to yield positive signals.

PlyC and its derivatives (such as a recombinant PlyC, recombinant PlyCA, recombinant PlyCB mutants) can be used to release Strep A antigens from Strep A bacteria for diagnostics. In one embodiment, recombinant PlyC holoenzyme is used at a concentration from 0.1 µg/mL to 80 µg/mL in an extraction solution. The extraction solution additionally contains, in some embodiments, salts to maintain the solution at a pH value in the range of 6-8, sugars (sucrose and/or trehalose), carrier proteins (casein and/or methylated BSA), detergents. In some embodiments, the extraction solution can even further include an antibody (polyclonal/monoclonal) specific to Strep A antigens coupled with microbeads (europium chelate-impregnated microbeads, or colored or magnetic microbeads) or gold sol, or carbon microparticles.

The extraction solution can be lyophilized, or dried down, to maintain the integrity of the components and the extraction capacity during the storage at 2-8° C. or room temperature. The lyophilized cake, or dried powder, can be rehydrated before testing. Rehydration of the extraction reagent can be achieved with transfer medium, a buffer solution, or water.

Prior to using an assay or diagnostic device to detect the existence or absence of Strep A in a biological sample, the biological sample is treated with the extraction reagent to release Strep A antigens, if any, from the cell. The extraction reagent contemplated herein is an enzymatic extraction reagent; in other words it is a non-chemical extraction reagent and does not use a small molecule chemical substance to treat the biological sample. Instead, the extraction reagent herein comprises an enzyme for the enzymatic extraction of the antigenic components from the Group A *Streptococcus* (GAS) bacteria.

The enzymatic extraction utilizes an enzymatic extraction agent, either in the form of a lyophilized or dried composition or in the form of liquid composition, comprising PlyC or a derivative thereof (such as a recombinant PlyCA or recombinant PlyCB mutant). In some embodiments, the lyophilized or dried composition further comprise a salt, a sugar, a carrier protein (such as casein and/or methylated BSA), and/or detergents. In some embodiments, the lyophilized or dried composition even further comprises an antibody (polyclonal/monoclonal) specific to Strep A antigens coupled with microbeads (europium chelate-impregnated microbeads, or colored or magnetic microbeads) or gold sol, or carbon microparticles. In some embodiments, the salt is selected from sodium chloride, sodium phosphate, ammonium phosphate, magnesium sulfate, sodium acetate, sodium lactate, sodium succinate, sodium propionate, and potassium phosphate. In some embodiments, the sugar is selected from trehalose, sucrose, maltose, fructose, raffinose, lactose, and glucose. In some embodiments, the detergent is selected from TWEEN 20, zwittergent, TRITON X-100, and PLURONIC F-68. The enzymatic extraction agent in the form of a liquid composition can be obtained by rehydrating the lyophilized or dried composition comprising PlyC or a derivative thereof as disclosed herein with a buffered solution (such as phosphate buffer, BIS-TRIS, MOPES, HEPES), water, or transfer medium (such as Amie's, Stuart, UTM).

The lyophilized or dried composition comprising PlyC or a derivative thereof can be prepared by lyophilizing an enzymatic extraction agent in the form of an aqueous composition comprising, in addition to PlyC or a derivative thereof in the amount ranging from 0.1 to 80 µg/mL, a salt to maintain the pH in the range of 6-8, a sugar, a carrier protein (such as casein and/or methylated BSA), and/or detergents. In some embodiments, the aqueous composition further comprises an antibody (polyclonal/monoclonal) specific to Strep A antigens coupled with microbeads (europium chelate-impregnated microbeads, or colored or magnetic microbeads) or gold sol, or carbon microparticles. In some embodiments, the salt is selected from sodium chloride, sodium phosphate, ammonium phosphate, magnesium sulfate, sodium acetate, sodium lactate, sodium succinate, sodium propionate, and potassium phosphate. In some embodiments, the sugar is selected from trehalose, sucrose, maltose, fructose, raffinose, lactose, and glucose. In some embodiments, the detergent is selected from TWEEN 20, zwittergent, TRITON X-100, and PLURONIC F-68.

In one embodiment, a method of using the extraction reagent is provided. In the method a specimen from a patient suspected of a Group A strep infection is provided. The patient specimens can be collected by, for example, a swab. The swab can be of any biological fluid, and examples include mouth, saliva, throat, lung, and nasal. The specimen swab can be tested directly by first rehydrating the lyophilized, or dried, extraction reagent then adding the swab directly to the extraction reagent. Alternatively, the specimen can be eluted from a swab into a transfer medium, which can then be used to rehydrate the extraction reagent.

The specimen (swab or the transfer medium) can be incubated in the rehydrated extraction solution containing PlyC (recombinant or mutant) for a period of about 10 seconds to 20 minutes, 30 seconds to 15 minutes, 30 seconds to 10 minutes, 1-10 minutes, 1-8 minutes, 1-6 minutes, 2-10 minutes, 2-8 minutes, 2-6 minutes, or less than about 10 minutes, less than about 8 minutes, less than about 6 minutes, or for about 5 minutes or less. After the extraction, the sample will be used as an antigen source for an immunoassay such as the Strep A lateral flow test strip, described in, for example, U.S. Pat. No. 5,770,460 and U.S. Application Publication No. 2013/0196337, both incorporated by reference herein.

In some embodiments, the enzymatic extraction method comprises mixing a biological sample containing or suspected of containing Strep A with the enzymatic extraction agent in the form of a liquid composition as disclosed herein. In some embodiments, the enzymatic extraction agent in the form of a liquid composition as disclosed herein is obtained by rehydrating the enzymatic extraction agent in the form of a lyophilized or dried composition as disclosed herein with a buffered solution, water, or transfer medium. In some embodiments, the method comprises eluting the biological sample into a transfer medium followed by mixing the transfer medium with the enzymatic extraction agent in the form of a lyophilized or dried composition as disclosed herein. In some embodiments, the method further comprises incubating the resulting mixture for a period of 1 to 10 minutes. At the completion of the extraction, the sample is applied to an immunoassay, such as a lateral flow based assay, for the signal detection.

In one embodiment, the anti-Strep A antibodies, such as the anti-Strep A antibodies coupled with microbeads (europium chelate-impregnated microbeads, or colored or magnetic microbeads) or gold sol, or carbon microparticles, can be present in the enzymatic extraction process, such as included in the enzymatic extraction agent disclosed herein. Thus, during the incubation time, the Strep A antigens present in the specimen are released from Strep A *Streptococcus* bacteria by PlyC enzyme extraction while interacting with the conjugated microbeads or microparticles coated with specific anti-Strep A antibodies. When the anti-Strep A antibody is included in the enzymatic extraction, the labeling zone in a lateral flow strip, such as those described herein, is no longer needed, or may not need to contain an anti-Strep A antibody.

Immunoassays for detection of Strep A that involves pre-treating a biological sample containing or suspected of containing Strep A with the enzymatic extraction agent as disclosed herein are contemplated, wherein the assay comprises a lateral flow device that allows for one-step pretreatment and detection of Group A *Streptococcus* organisms with enhanced specificity. Immunoassay devices are known in the art, and typically have at least a sample receiving zone, a labeling zone and a capture zone, and can be prepared according to the description in any of U.S. Pat. Nos. 5,415,994; 5,763,262 and 5,770,460, which are incorporated by reference in their entirety.

Molecular assays for detection of Strep A are contemplated, where the assay comprises an extraction reagent to treating a biological sample containing or suspected of containing Strep A and a contained with reagents for molecular amplification of a target sequence of the Strep A antigen. In one embodiment, the reagents for amplification of the target sequence are for thermal amplification, and in another embodiment, the reagents for amplification are for isothermal amplification, such as helicase dependent amplification. The reagents for molecular amplification are well known to a skilled artisan and include a suitable enzyme for separating the strands of DNA, reverse and forward primers, and a labelled probe that binds an amplicon.

Accordingly, in one aspect of the disclosure, a device is provided for detecting the presence of Strep A in a sample. Various embodiments of a device are contemplated, and exemplary embodiments are described herein for the purposes of illustration. A skilled artisan will appreciate, however, that the illustrative embodiments are non-limiting to the inventive concepts set forth herein.

In one embodiment, a device comprises a series of zones in fluid communication. In a preferred embodiment, a sample receiving zone is in fluid communication with second and subsequent zones, such as a labeling zone, a capture zone, and/or an absorption zone. A first embodiment of a device is depicted in FIG. 1, which shows an immunoassay test strip for detection of Group A *Streptococcus*. An exemplary test strip 10 is comprised of a support layer 12 that preferably extends the length of the test strip. Support layer 12 supports in series a sample pad 14, a label pad 16, a nitrocellulose member 17, and an optional absorbent pad 18. On the nitrocellulose member is a test line 20 and a control line 22. For detection of Strep A, the label pad comprises anti-Strep A antibodies, as does the test line. In one embodiment, the anti-Strep A antibodies are coupled with microbeads (europium chelate-impregnated microbeads, or colored or magnetic microbeads) or gold sol, or carbon microparticles. In one embodiment, the antibodies deposited on the label pad comprise a label which aids or permits detection of the antibody. The labeled antibody specifically binds the Strep A antigen as it passes through the label zone. The capture zone comprises a means for specifically binding the labeled antigen thereon. In one embodiment, the biological sample is contacted with N-acetyl-D-glucosamine (NAG) prior to application to the device and/or during its flow through the device. In one embodiment, NAG can be incorporated into the device, such as in the sample receiving zone, the labeling zone, or both, and/or the sample can be treated with NAG prior to its application to the sample receiving zone of device.

In the embodiments when the enzymatic extraction agent further comprising an antibody (polyclonal/monoclonal) specific to Strep A antigens coupled with microbeads (europium chelate-impregnated microbeads, or colored or magnetic microbeads) or gold sol, or carbon microparticles is used to extract and release Strep A antigens from the cell, the labeling zone in the device is not needed.

Figure 2:
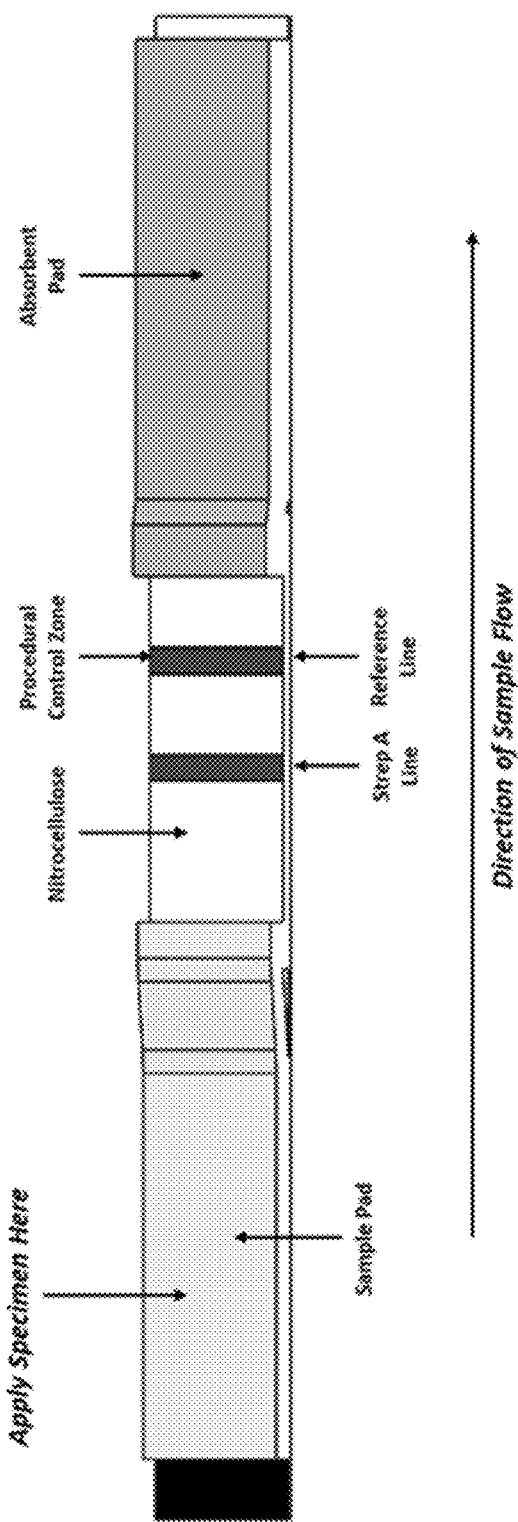
FIG. 2 illustrates another exemplary immunoassay device.

Thus, an alternative device is depicted in FIG. 2. FIG. 2 depicts a test strip without a labeling zone. This device can be used when the enzymatic extraction agent further comprises an antibody (polyclonal/monoclonal) specific to Strep A antigens coupled with microbeads (europium chelate-impregnated microbeads, or colored or magnetic microbeads) or gold sol, or carbon microparticles.

In one embodiment, the lateral flow immunoassay comprises an immunoassay with label that can be read visually with the unaided eye, such as a colored bead or particle, wherein a collection of such beads or particles at the test line of the immunoassay can be viewed by a user with the naked eye. In another embodiment, the lateral flow immunoassay comprises an immunoassay with a label that is read by an instrument or by an eye with the aid of an instrument. For example, a fluorescent label in the immunoassay is detected using an instrument that can excite the label and the excited label can be read with the instrument, with the eye aided by instrument or with the eye. An exemplary instrument and lateral flow immunoassay is described in U.S. Pat. No. 9,207,181, which is incorporated by reference herein.

In another aspect, a device is provided for detecting the presence of Strep A in a sample, wherein the device comprises a matrix having (i) a sample receiving zone for receiving a Strep A-specific antigen sample, wherein the Strep A-specific antigen sample is obtained by the enzymatic extracting method disclosed herein, (ii) a labeling zone containing an antibody for specifically labeling the antigen as it passes there through and/or (iii) a capture zone having means for specifically binding the labeled antigen thereon, wherein the sample receiving zone, the labeling zone and the capture zone are arranged on the matrix in a liquid flow path. In some embodiments, the sample receiving zone, the labeling zone, or both contain a blocking reagent. In some embodiments, the antibody contained in the labeling zone is an anti-Strep A antibody coupled with microbeads (europium chelate-impregnated microbeads, or colored or magnetic microbeads) or gold sol, or carbon microparticles.

Another embodiment of a device contemplated for use is described in U.S. Pat. No. 5,415,994, which is incorporated by reference herein. In this embodiment, the device comprises a receiving chamber positioned or positionable for fluid contact with a lateral flow immunoassay device, and preferably positioned for fluid communication with a sample receiving zone or a labeling zone of the immunoassay test strip. The biological sample suspect of containing Strep A is received into the receiving chamber, such as by insertion of a swab containing the sample or by dispensing an aliquot of the sample into the receiving chamber. One or more enzymatic extraction agent as disclosed herein can be additionally added to the receiving chamber or to the swab. In one embodiment, the enzymatic extraction agent further comprises a blocking reagent. In one embodiment, the receiving chamber is positioned over the sample receiving zone is dimensioned for receiving a liquid enzymatic extraction reagent comprising a blocking reagent, and, optionally comprises a cylindrical portion for receiving a swab containing a patient sample. The immunoassay test strip comprises a matrix having a sample receiving zone for receiving the extraction liquid containing the treated sample suspected of comprising Strep A antigen, a labeling zone having a polyclonal antibody for specifically labeling the antigen as it passes there through and a capture zone having means for specifically binding the labeled antigen thereon, wherein the sample receiving zone, the labeling zone and the capture zone are arranged on the matrix in a liquid flow path. In some embodiments, the polyclonal antibodies are coupled with microbeads (europium chelate-impregnated microbeads, or colored or magnetic microbeads) or gold sol, or carbon microparticles.

In some embodiments of the devices described herein, the enzymatic extraction agent provided to treat the biological sample also contains a blocking reagent, such as NAG.

In another aspect, a method is provided for detecting the presence or absence of Strep A in a sample, comprising (a) providing a matrix having (i) a sample receiving zone for receiving a Strep A-specific antigen sample, (ii) a labeling zone containing an antibody for specifically labeling the antigen as it passes there through and (iii) a capture zone having means for specifically binding the labeled antigen thereon, wherein the sample receiving zone, the labeling zone and the capture zone are arranged on the matrix in a liquid flow path, and (b) contacting the sample receiving zone with the sample, wherein said sample, prior to contacting, is treated with a liquid enzymatic extraction agent disclosed herein which further comprises a blocking reagent; and (c) detecting the presence or absence of the antigen in the capture zone. In one embodiment, the matrix additionally comprises an absorbent zone downstream of the capture zone. In one embodiment, the antibody contained in the labeling zone is coupled with microbeads (europium chelate-impregnated microbeads, or colored or magnetic microbeads) or gold sol, or carbon microparticles.

In another aspect, a method is provided to reduce the false positive rate of a lateral flow assay in the detection of Group A *Streptococcus* in a liquid sample, wherein, in the lateral flow assay, NAG-binding components of a polyclonal antibody label used in the assay are preferentially bound, the method comprising treating a bibulous matrix with an amount of NAG effective as a blocking agent to enhance the specific binding of the polyclonal antibody to Strep A antigen and reduce the false positive rate of the assay. In some embodiments, the polyclonal antibody is coupled with microbeads (europium chelate-impregnated microbeads, or colored or magnetic microbeads) or gold sol, or carbon microparticles.

In some embodiments, the sample is collected through the use of a pharyngeal swab. In some embodiments, the sample is collected through a swab of the pharynx, tongue, cheek, teeth, gums or nasal passages. In some embodiments, a body fluid is sampled, such as urine, saliva, sputum, mucous, blood, blood components such as plasma or serum, amniotic fluid, semen, wound secretions, vaginal secretions, tears, spinal fluid, washings, and other bodily fluids. Included among the sample are swab specimens from, e.g., the cervix, urethra, nostril, and throat.

In some embodiments, the first antibody is a polyclonal antibody that binds to one or more epitopes of Group A *Streptococcus*, and also binds to NAG. In some embodiments, the antibody is a population of polyclonal antibodies, the population including a portion of antibodies having specific binding to NAG. In some embodiments, the antibody does not bind to glucosamine, galactosamine, mannosamine, acetyl-muramic acid, chitin, chitosan, and/or hyaluronic acid (e.g., HA-50K). In some embodiments, each of the aforementioned antibodies is coupled with microbeads (europium chelate-impregnated microbeads, or colored or magnetic microbeads) or gold sol, or carbon microparticles.

In some embodiments, the antibody has high specificity and low sensitivity for detecting a Group A *Streptococcus* antigen. In some embodiments, the antibody has high sensitivity and low specificity for detecting a Group A *Streptococcus* antigen. In some embodiments, the antibody has high specificity and high sensitivity for detecting a Group A *Streptococcus* antigen. In some embodiments, each of the aforementioned antibodies is coupled with microbeads (europium chelate-impregnated microbeads, or colored or magnetic microbeads) or gold sol, or carbon microparticles.

Examples of the antibodies used in the immunoassay of the present disclosure may include, but are not limited to a polyclonal antibody, such as an affinity purified rabbit anti-Strep A antibody. In some embodiments, the antibody is coupled with microbeads (europium chelate-impregnated microbeads, or colored or magnetic microbeads) or gold sol, or carbon microparticles.

Illustrative publications describing components of precursor compositions, methods and kits, as well as various antibodies for detecting Group A *Streptococcus* include the following: U.S. Pat. Nos. 5,415,994; 5,763,262 and 5,770,460. All of these patents, applications and publications are incorporated by reference herein, in their entirety.

Four studies, which involve treating Strep A bacterial with an enzymatic extraction agent, were conducted to detect Strep A bacterial using a lateral flow strip. Studies 1, 2, and 4 used the enzymatic extraction agent in the form of a liquid composition comprising PlyC and a test strip assay wherein the fluorescent microbeads coated with a specific anti-Strep A antibody was dried on the label pad. In Study 3, the enzymatic extraction agent in the form of a liquid composition was prepared by rehydrating the lyophilized extraction reagent containing the recombinant PlyC and the fluorescent microbeads coated with specific anti-Strep A antibodies, and the strip did not contain a labeling zone with dried fluorescent microbeads coated with a specific anti-Strep A antibody. Study 4 used bacteria other than Strep A to show good selectivity of the composition and method.

An additional study, namely, Study 5, compared an assay using the enzymatic extraction method disclosed herein with an assay using a known chemical extraction method.

Figure 3:
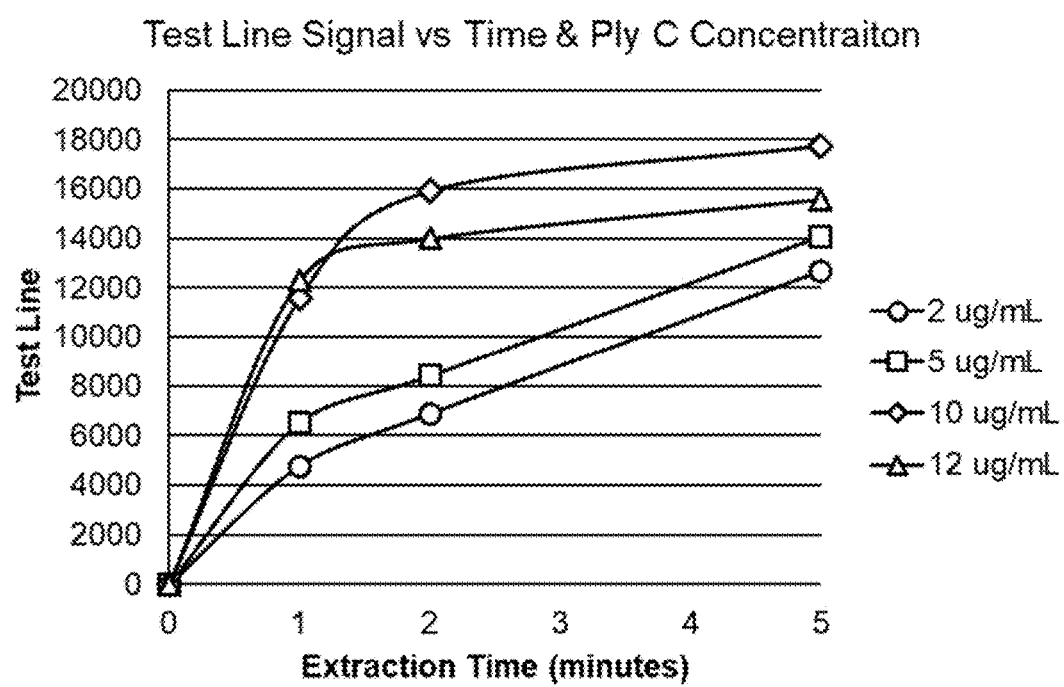
FIGS. 3-5 show the signal at the test line in Strep A immunoassay devices for Strep A samples versus either extraction time or amount of Strep A, using the enzymatic extraction method disclosed herein.

FIG. 3 shows the results obtained from Study 1 where the Strep A signal detected as a function of extraction time up to 5 minutes is shown. The strength of signal increased with the extraction time and amount of Strep A.

Figure 4:
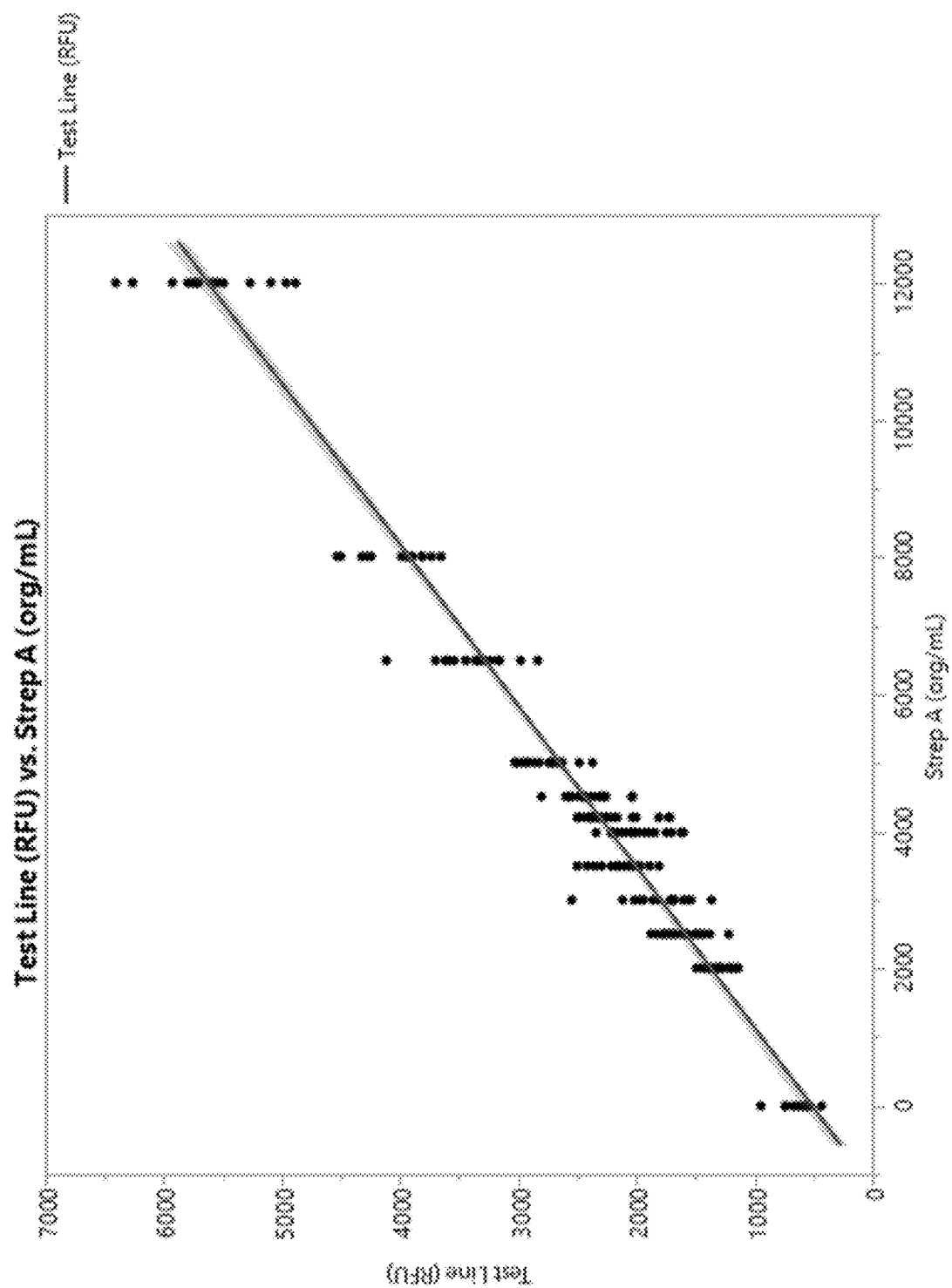
Figure 5:
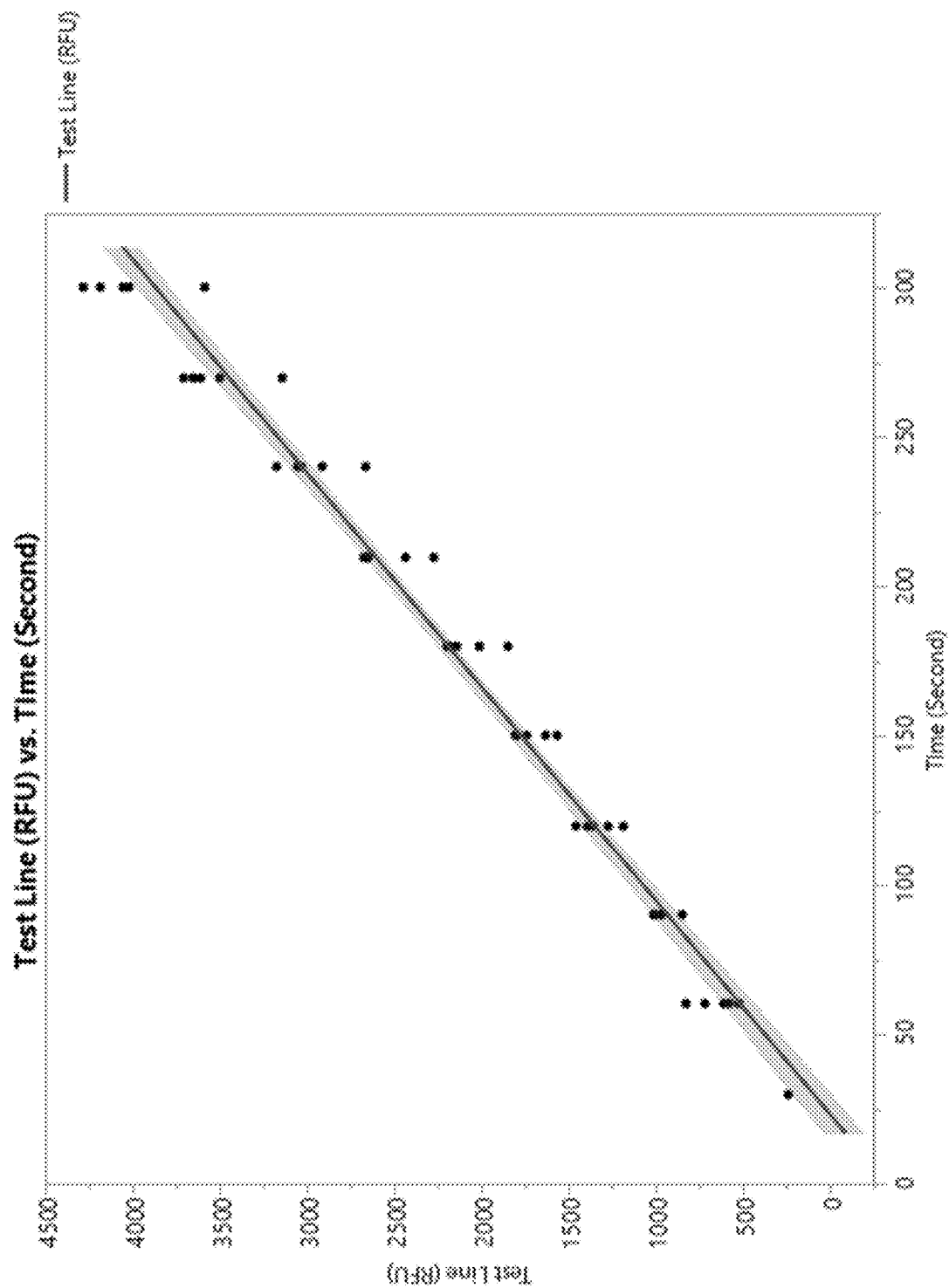

The data in FIG. 4 and FIG. 5, obtained from Study 2 and Study 3, respectively, show the Strep A signal versus the known Strep A concentration and the Strep A signal versus extraction time were almost linear.

Figure 6:
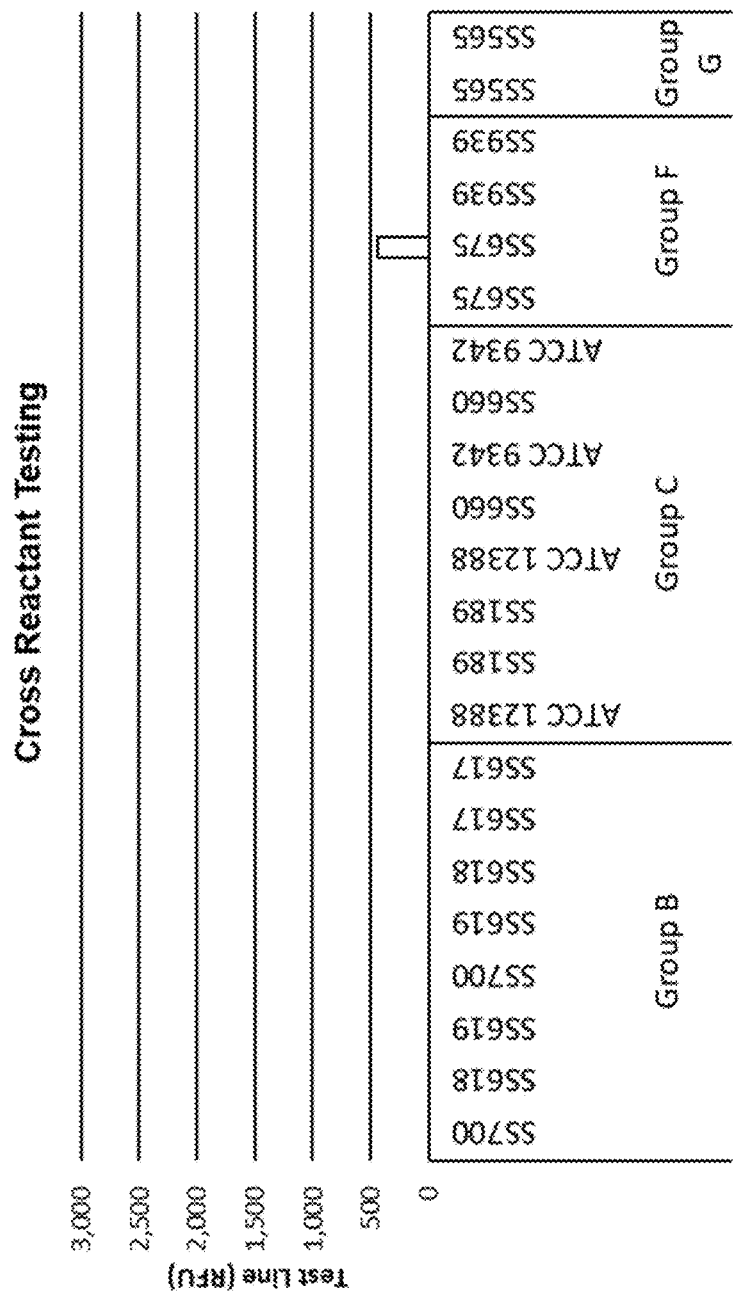
FIG. 6 is a bar graph showing the signal at the test line for Group B, C, F and G *Streptococcus* bacteria.

FIG. 6 shows the data from Study 4 and demonstrates the negative results for detection of Group B, C, and G *Streptococcus* bacteria and weak signal for Group F *Streptococcus* bacteria. This demonstrates good selectivity of the composition and method disclosed herein.

Figure 7:
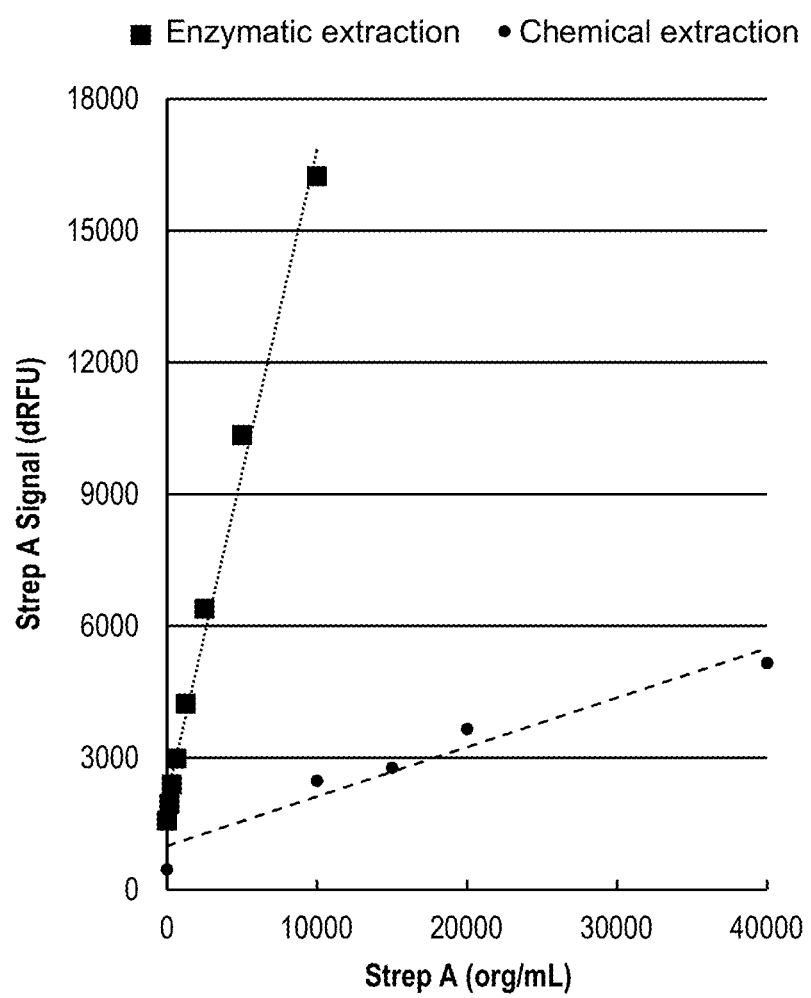
FIG. 7 is a chart showing that an assay using enzymatic extraction method disclosed herein provided more sensitive detection than an assay using a known chemical extraction.

FIG. 7 shows the results obtained from Study 5. FIG. 7 demonstrates that the assay which used Strep A antigen sample obtained from Strep A bacterial sample treated with the enzymatic extraction agent disclosed herein is about 20 times more sensitive than that treated with a known chemical extraction agent.

Kits

Kits comprising an assay as described herein are also contemplated. In one embodiment, the kit comprises (i) an immunoassay device or a container with reagents, such as primers and probes, for detection of Strep A antigen and (ii) an extraction reagent comprising PlyC. The kits may additionally include any one or more of written instructions for using the device or container and/or collecting a biological sample, an instrument or tool for collecting a biological sample, labels for marking the device or container, and other containers or vials containing a reagent for preparing a treated sample. The kits may additionally include instructions for reading and interpreting the results of an assay. The kits may further comprise reference samples that may be used to compare test results with the specimen samples. In one embodiment the kits include a swab for collecting a biological sample, and instructions for use of the assay and for collecting the sample, wherein the instructions do not contain a caution against contacting, for example, one or more of the back of the throat, tonsils, cheek or tongue.

Accordingly, in another aspect, a kit is provided, comprising (a) a device comprising a matrix having (i) a sample receiving zone for receiving a sample containing or suspected of containing a Group A *Streptococcus*-specific antigen, (ii) a labeling zone containing an antibody for specifically labeling the antigen as it passes there through and (iii)

a capture zone having means for specifically binding the labeled antigen thereon, and, optionally (iv) an absorbent zone, wherein the sample receiving zone, the labeling zone and the capture zone (and the optional absorbent if present) are arranged on the matrix in a liquid flow path; and (b) a container comprising an enzymatic extraction agent disclosed herein, which may further include an antibody for specifically labeling the antigen. In some embodiments, at least one of the enzymatic extraction agent, the sample receiving zone and the labeling zone contain a blocking reagent. In some embodiments, the antibody is coupled with microbeads (europium chelate-impregnated microbeads, or colored or magnetic microbeads) or gold sol, or carbon microparticles.

EXAMPLES

The following examples describe exemplary assays that can be performed using the presently disclosed methods and compositions. However, the present disclosure shall in no way be considered to be limited to the particular embodiments described below.

Example 1: IMMUNOASSAY USING ENZYMATIC EXTRACTION

Enzymatic extraction procedures generally comprise (1) dispensing the enzymatic extraction agent in the form of a liquid composition into a reagent tube, gently swirling the reagent tube to dissolve the contents, (2) placing the patient swab sample into the reagent tube, rolling the swab at least three times while pressing the head against the bottom and side of the reagent tube, leaving the swab in the reagent tube for two minutes or more, (3) rolling the swab head against the inside of the reagent tube before disposing of the used swab in a biohazard waste, (4) filling a pipette with about 120 µL of the extracted patient sample from the reagent into the receiving zone of a lateral flow strip, (5) developing the testing for about 5 minutes and observe the result. In case the patient swab is placed in a transport media, step (2) comprises transferring about 400 µL of the patient sample from the transport media tube using a pipette into the reagent tube, gently swirling the reagent tube to mix and incubate for two (2) minutes or more.

Study 1: Strep A bacteria (Strain Bruno 19615) samples at $5\times10^4$ org/mL were extracted with an enzymatic extraction agent in the form of liquid composition containing various concentrations of recombinant PlyC (Quidel) for a total 5-minute extraction time and the extracted samples were detected on the strip with the fluorescent microbeads coated with specific anti-Strep A antibodies dried on the label pad. The test line signals versus extraction time are shown in FIG. 3.

Study 2: Various concentrations of Strep A bacteria (Strain Bruno 19615) samples were extracted by an extraction agent in the form of liquid composition containing the recombinant PlyC (Quidel) at a concentration of approximately 10 µg/mL for a total 5-minute extraction time and the extracted samples were detected on the strip with the fluorescent microbeads coated with specific anti-Strep A antibodies dried on the label pad. The test line signals versus concentrations of Strep A bacteria are shown in FIG. 4.

Study 3: Strep A bacteria (Strain Bruno 19615) samples at 1e4 org/mL were extracted in an enzymatic extraction agent in the form of a liquid composition prepared by rehydrating the lyophilized extraction reagent containing the recombinant PlyC (approximate concentration of 10 µg/mL) and the microbeads coated with specific anti-Strep A antibodies for a total 5-minute extraction time. The extracted samples were detected on the strip without the fluorescent microbead containing label pad. The test line signals vs. incubation time are shown in FIG. 5.

Study 4: Various Groups of *Streptococcus* bacteria (Group B, C, F and G) samples at concentrations above 5.8e7 CFU/mL were tested using the formulated extraction solution containing the recombinant PlyC (approximate concentration of 10 µg/mL) for a total 5-minute extraction time. The extracted samples were detected on the strip with the fluorescent microbeads coated with specific anti-Strep A antibodies dried on the label pad. The test line signals are shown in FIG. 6.

Study 5: Various concentrations of Strep A bacteria samples were extracted in a rehydrated extraction agent containing the recombinant PlyC at a concentration of approximately 10 µg/mL and the fluorescent microbeads coated with the specific anti-Strep A antibodies for a total 2-minute extraction time. The extracted samples were detected on the strip composed of an absorbent pad, sample pad and nitrocellulose membrane on which the specific anti-Strep A antibodies were spotted. The test line signals versus concentrations of Strep A bacteria are shown in the table below and in FIG. 7. The data indicate that the assay based on PlyC enzymatic extraction is much more sensitive than the assay based on a known chemical extraction and can detect a lower level of Strep A bacteria analytically.

| | Strep A Bacteria Conc. (org/mL) | Test Line Fluorescent Intensity (RFU) |
|---|---|---|
| Assay based on PlyC enzymatic extraction | 0 | 1571 |
| | 313 | 2398 |
| | 625 | 2986 |
| | 1250 | 4236 |
| | 2500 | 6400 |
| | 5000 | 10351 |
| Assay based on chemical extraction | 0 | 456 |
| | 10000 | 2478 |
| | 15000 | 2774 |
| | 20000 | 3655 |
| | 40000 | 5159 |

Example 2: MOLECULAR ASSAY USING ENZYMATIC EXTRACTION

A sample suspected of comprising Strep A bacterial is obtained from a human subject. The sample is treated with an extraction reagent comprising PlyC, where the extraction reagent is in liquid form. The sample and the extraction reagent are mixed and allowed to incubate at room temperature for five minutes, to form a treated sample.

Next, an aliquot of the treated sample is placed in a reaction tube that contains lyophilized reagents for helicase dependent amplification, deoxyribose nucleotide triphosphates (dNTPs), primers and probes specific for amplification and detection of the Group A Strep target. A rehydration buffer is added and the reaction tube is placed in an instrument for amplification and detection of the target sequence (SOLANA®, Quidel Corporation). Detection of Group A Strep is reported by the instrument.

While various specific embodiments have been illustrated and described, skilled artisans will recognize various modifications, permutations, additions and sub-combinations thereof, and will appreciate that these can be made without departing from the spirit and scope of the present disclosure.

Therefore, it is to be understood that the disclosure is not to be limited to the specific embodiments disclosed herein, as such are presented by way of example. Although specific terms are employed herein, they are used in a generic and descriptive sense only and not for purposes of limitation.

All literature and similar materials cited in this application, including, but not limited to, patents, patent applications, articles, books, treatises, internet web pages and other publications cited in the present disclosure, regardless of the format of such literature and similar materials, are expressly incorporated by reference in their entirety for any purpose to the same extent as if each were individually indicated to be incorporated by reference. In the event that one or more of the incorporated literature and similar materials differs from or contradicts the present disclosure, including, but not limited to defined terms, term usage, described techniques, or the like, the present disclosure controls.

What is claimed is:

1. An enzymatic extraction agent comprising a recombinant multimeric PlyC holoenzyme consisting of PlyCA and PlyCB gene products and a labeled antibody that specifically binds to a Strep A antigen.

2. The enzymatic extraction agent of claim 1, wherein the antibody is coupled to microbeads, gold sol, or carbon microparticles.

3. A device for detecting the presence of Group A *Streptococcus* in a test sample, the device comprising:
a matrix having (i) a sample receiving zone for receiving a test sample containing or suspected of containing a Group A *Streptococcus*-specific antigen, wherein the test sample comprises is the biological sample and an enzymatic extraction agent comprising a recombinant multimeric PlyC holoenzyme consisting of PlyCA and PlyCB gene products and a labeled antibody that specifically binds to the Group A *Streptococcus*-specific antigen and (ii) a capture zone having means for specifically binding a labeled Group A *Streptococcus*-specific antigen thereon, wherein the sample receiving zone and the capture zone are arranged on the matrix in a liquid flow path.

4. The device of claim 3, wherein the sample receiving zone comprises N-acetyl-D-glucosamine (NAG).

5. The device of claim 3, wherein the antibody is a polyclonal, monoclonal, or recombinant chimeric antibody coupled to fluorescent microbeads.

6. The device of claim 3, wherein the antibody is coupled to europium chelate-impregnated microbeads.

7. The device of claim 3, wherein the means for specifically binding the labeled Group A *Streptococcus*-specific antigen is a capture antibody.

8. The device of claim 7, wherein the capture antibody is a polyclonal, monoclonal, or recombinant chimeric antibody.

9. A kit comprising:
a device comprising a matrix having (i) a sample receiving zone for receiving a test sample containing or suspected of containing a Group A *Streptococcus*-specific antigen and (ii) a capture zone having means for specifically binding a labeled Group A *Streptococcus*-specific antigen thereon, wherein the sample receiving zone and the capture zone are arranged on the matrix in a liquid flow path; and
a container comprising the enzymatic extraction agent of claim 1.

10. The kit of claim 9, wherein the antibody is coupled to europium chelate-impregnated microbeads.

11. The kit of claim 9, wherein at least one of the enzymatic extraction agent or the sample receiving zone comprise N-acetyl-D-glucosamine (NAG).

12. The kit of claim 11, wherein the NAG is deposited on the sample receiving zone.

13. A kit comprising:
a device comprising a matrix having (i) a sample receiving zone for receiving a test sample containing or suspected of containing a Group A *Streptococcus*-specific antigen, wherein the test sample comprises a biological sample and the enzymatic extraction agent of claim 1 and (ii) a capture zone having means for specifically binding a labeled Group A *Streptococcus*-specific antigen thereon, wherein the sample receiving zone and the capture zone are arranged on the matrix in a liquid flow path;
a container comprising the enzymatic extraction agent of claim 1;
an instrument for collecting the biological sample; and
instructions for use.

14. The kit of claim 13, wherein the instrument is a swab.

15. The kit of claim 13, wherein the instructions do not caution to not touch tongue, sides or top of mouth with the instrument when collecting a sample.

16. The enzymatic extraction agent of claim 2, wherein the microbeads are fluorescent microbeads, europium chelate-impregnated microbeads, colored microbeads, or magnetic microbeads.

17. The enzymatic extraction agent of claim 1, wherein the extraction agent is in the form of a liquid, lyophilized or dried composition.

18. The enzymatic extraction agent of claim 17, wherein the extraction agent is in the form of a liquid and the recombinant PlyC holoenzyme is present at a concentration from 0.1 µg/mL to 80 µg/mL.

19. The kit of claim 13, wherein the enzymatic extraction agent is in the form of a liquid and the recombinant PlyC holoenzyme is present at a concentration from 0.1 µg/mL to 80 µg/mL.

20. The enzymatic extraction agent of 1, wherein the recombinant multimeric PlyC holoenzyme consists of a single PlyCA protein bound to the PlyCB octamer.

21. The device of claim 3, wherein the biological sample is collected on a swab.

22. The device of claim 3, wherein the biological sample is a liquid sample.

23. The device of claim 22, wherein the liquid sample is a body fluid.

24. The device of claim 23, wherein the body fluid is urine, saliva, sputum, mucus, plasma, serum, amniotic fluid, semen, vaginal secretion, tear, spinal fluid, or body washing.

25. The device of claim 3, wherein the biological sample is a solid or semi-solid sample.

26. The device of claim 25, wherein the solid or the semi-solid sample is feces, biopsy specimen, or skin.

27. The device of claim 21, wherein the sample is eluted from the swab into a transfer medium.

* * * * *